United States Patent [19]

Evenson et al.

[11] 4,073,785

[45] Feb. 14, 1978

[54] CERTAIN AS-TRIAZINO [4,3-a][1,4]BENZODIAZEPINE DERIVATIVES

[75] Inventors: Gerald Norman Evenson, Cooper Township, Kalamazoo County; Robert Bruce Moffett, Kalamazoo, both of Mich.

[73] Assignee: The Upjohn Company, Kalamazoo, Mich.

[21] Appl. No.: 775,725

[22] Filed: Mar. 9, 1977

[51] Int. Cl.² .............. C07D 243/20; C07D 401/04; C07D 487/04
[52] U.S. Cl. .................. 260/243.3; 260/239 BD; 260/296 B; 424/249
[58] Field of Search ................................ 260/248 AS

[56] References Cited

U.S. PATENT DOCUMENTS

| 3,818,003 | 6/1974 | Szmuszkovicz | 260/248 AS |
|---|---|---|---|
| 3,882,112 | 5/1975 | Szmuszkovicz | 260/248 AS |
| 3,933,816 | 1/1976 | Szmuszkovicz | 260/248 AS |
| 4,016,165 | 4/1977 | Moffett | 260/248 AS |
| 4,017,492 | 4/1977 | Moffett | 424/249 |
| 4,028,356 | 6/1977 | Moffett | 260/248 AS |

OTHER PUBLICATIONS

Moffett IV, Letters on Heterocyclic Chemistry, vol. 3, pp. 3449-3456, (1976).

*Primary Examiner*—Alton D. Rollins
*Attorney, Agent, or Firm*—Hans L. Berneis

[57] ABSTRACT

Compounds of the formula IV

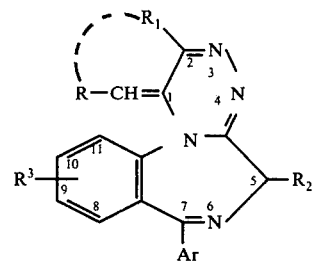

wherein R is hydrogen or alkyl of 1 or 2 carbon atoms; wherein $R_1$ is alkyl of 1 to 3 carbon atoms, inclusive; or

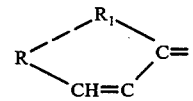

is a 2-cycloalkenylene ring of 5 or 6 carbon atoms; wherein $R_2$ is hydrogen, methyl or ethyl; wherein $R_3$ is hydrogen, fluoro, chloro, bromo, nitro and $-CF_3$; and wherein Ar is phenyl, o-chlorophenyl, o-fluorophenyl, 2,6-difluorophenyl, and 2-pyridyl, are prepared by treating a hydrazino compound of the formula:

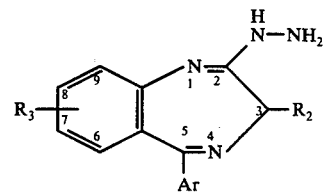

wherein Ar and $R_3$ are defined as above, with a dicarbonyl compound II:

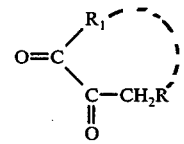

and cyclizing the resulting compound III to give the compound IV above.

Compound IV, including the pharmacologically acceptable acid addition salt of these compounds, have sedative, anxiolytic and muscle-relaxing activity and can be used for the treatment of anxieties or muscle strains of mammals, including man.

16 Claims, No Drawings

CERTAIN AS-TRIAZINO [4,3-A][1,4]BENZODIAZEPINE DERIVATIVES

BACKGROUND OF THE INVENTION

Field of the Invention

This invention is directed to new organic compounds and is particularly concerned with as-triazinobenzodiazepines of formula IV, intermediates thereto of formula III, and the process therefor.

The novel compounds and process of production therefor can be illustratively represented as follows:

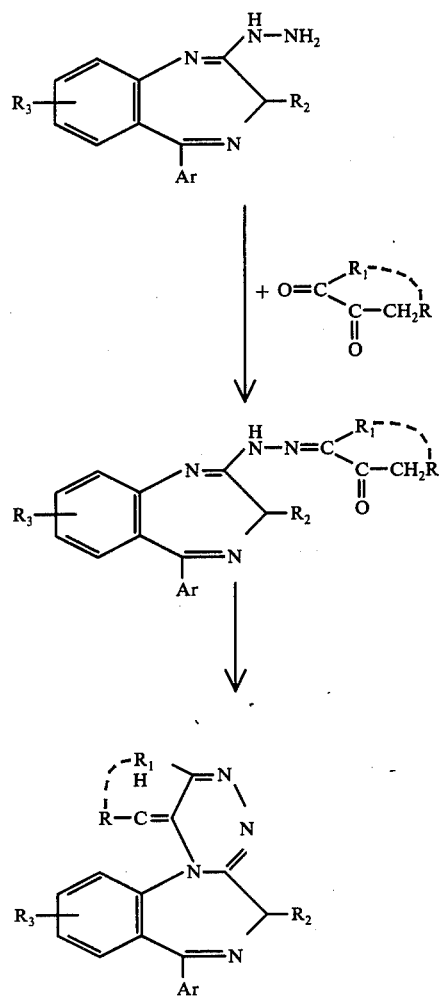

wherein R is hydrogen or alkyl of 1 to 2 carbon atoms, inclusive; wherein $R_1$ is alkyl of 1 to 3 carbon atoms, inclusive, or the group

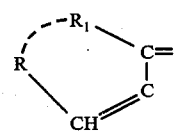

is a 2-cycloalkylene ring of 5 or 6 carbon atoms and the group

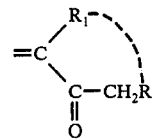

is 2-oxocyclopentylidene or 2-oxocyclohexylidene; wherein $R_2$ is hydrogen, methyl or ethyl; wherein $R_3$ is hydrogen, fluoro, chloro, nitro and $-CF_3$; and wherein Ar is phenyl, o-chlorophenyl, o-fluorophenyl, 2,6-difluorophenyl, and 2-pyridyl.

The process of this invention comprises: treating a hydrazino compound of formula I with a dicarbonyl reagent of formula II to obtain the corresponding compound of formula III; and treating compound III with a cyclizing reagent to obtain the corresponding compound of formula IV.

The invention claims the compounds of formula IV and the pharmacologically acceptable acid addition salts thereof, the intermediates of formula III, and the process to make these compounds.

DESCRIPTION OF THE PREFERRED EMBODIMENT

Alkyl groups of 1 to 3 carbon atoms, inclusive, are exemplifid by methyl, ethyl and propyl.

The more preferred compounds of this invention are of the formulae IIIA and IVA:

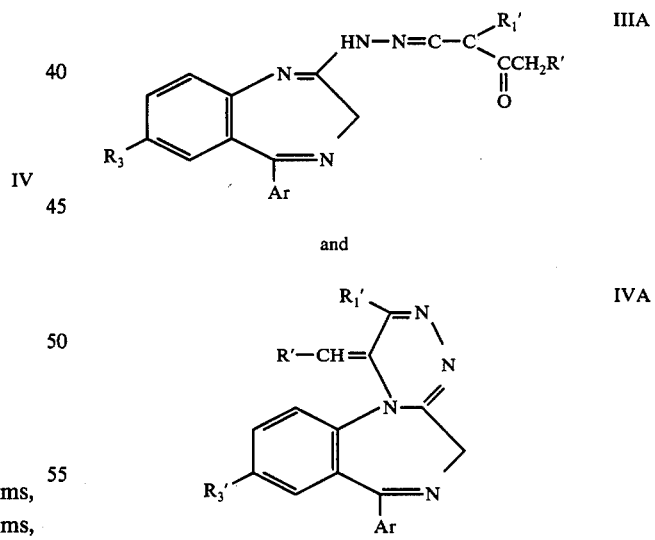

wherein R' is hydrogen or methyl, $R_1'$ is methyl or ethyl; wherein $R_3'$ is fluoro, chloro, bromo, or trifluoromethyl; and wherein Ar is phenyl, o-chlorophenyl, o-fluorophenyl, 2,6-difluorophenyl or 2-pyridyl, and the pharmacologically acceptable acid addition salts of compound IVA.

The most preferred compounds of this invention are of the formula 111B and IVB:

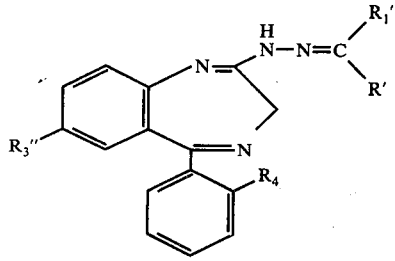

and

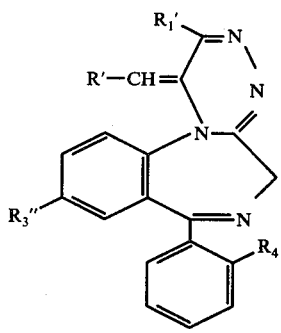

wherein $R_1'$ is methyl or ethyl; wherein $R'$ is hydrogen or methyl; wherein $R_3''$ is fluoro, chloro or trifluoromethyl; and wherein $R_4$ is hydrogen, chloro or fluoro, and the pharmacologically acceptable acid addition salts of compound IVB.

Compounds of formula IV (including IVA and IVB) are sedative, tranquilizing, anxiolytic, muscle-relaxing and anti-convulsive agents which are useful for treating anxieties, convulsions or strained muscles in mammals, including man.

The sedative-tranquilizing-anxiolytic activity was evaluated in compounds of formula IV by the following test:

Gamma Butyrolactone Sleep Potentiation

Gamma-butyrolactone produces loss of righting in mice at doses higher than 400 mg./kg. intraperitoneally. At lower doses (200 mg./kg.) the mice do not lose their righting reflex unless previously treated with sub-hypnotic doses of central nervous system depressant agents. This then provides a technique to study the depressant activity of potential central nervous system agents. Method: The test compound is injected intraperitoneally 50 mg./kg. into a group of four mice and 30 minutes later gamma-butyrolactone is injected intraperitoneally, 200 mg./kg. (normally a sub-hypnotic dose). After 10 minutes, the mice are tested for loss of righting reflex. If more than two mice show a loss of righting for 1 minute or more, the compound is retested at multiple dose levels.

Anti-convulsion Test:

Protection Against Bicucullin-Induced Tonic Extensor Convulsions

In this procedure, groups of four Carworth Farms male mice, weighing 18–22 g. each, are injected intraperitoneally with the test agent prepared in 0.25% methylcellulose. Thirty minutes later, bicucullin in injected intravenously at 1 mg./kg. Bicucullin is solubilized in 1N hydrochloric acid and diluted to a concentration of 1–4 mg./ml. with physiological saline and adjusted to a final pH of 5–6 before injection. Mice are observed for 5 minutes after bicucullin injection. A compound is considered to be active if it protects at least 2 of the four mice from tonic extensor convulsions during this period. Active compounds are retested using multiple dose levels decreasing at 0.3 or 0.5 log intervals and the number of mice failing to convulse is used as a quantal response to calculate the $ED_{50}$ (Spearman and Karber: Finney, D. J., Statistical Method in Biological Assay, Hafner Publ. Co., N.Y., p. 524, 1952). This procedure is a useful test for detecting compounds with minor tranquilizer or sedative activity.

Anti-convulsant, Muscular Relaxing Activity by the Pentylene-tetrazol (Metrazol) Test Metrazol Induced Convulsion Test:

The test compound is injected intraperitoneally (50 mg./kg.) into groups of four mice at multiple dose levels decreasing in 0.3 log intervals. Thirty minutes later Metrazol is injected subcutaneously (at the nape of the neck), 85 mg./kg. Fifteen minutes later a set of keys is rattled over the cage to induce the clonic convulsions. The number of mice protected against convulsions and death is recorded.

The compounds IV of this invention have positive results in these tests.

Thus, these compounds are useful for tranquilization, sedation, treating anxieties, and also useful as anti-convulsants and muscle-relaxants in mammals and birds.

The pharmaceutical forms contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, corn starch, stearic acid, methylcellulose and the like may be used as carriers or for coating purposes. Water or oil, e.g., coconut oil, sesame oil, safflower oil, cottonseed oil, peanut oil may be used for preparing solutions or suspensions of the active drug. Sweetening, coloring and flavoring agents may be added.

For mammals and birds, food premixes with starch, oatmeal, dried fishmeat, fishmeal, flour and the like can be prepared.

The compounds of formulae III and IV can be used in dosages of 0.05–2 mg./kg./day; preferably in unit dosages of 0.1–1.0 mg./kg./day in oral or injectable preparations as described above, to alleviate tension and anxiety, muscle spasm or convulsions in mammals, including man, or birds.

The starting materials of formula I of this invention, with a 5-phenyl- or substituted phenyl groups, are known in the art, e.g., from Canadian Pat. No. 908,657.

The compounds of formula I which have a 2-pyridyl group in the 5-position can be made from the corresponding 2-thiones according to U.S. Pat. No. 3,996,230.

In carrying out the process of this invention, a compound of formula I is treated with a selected vicinal dione compound II such as 2,3-butanedione, 2,3-pentanedione, 2,3-hexanedione, or 1,2-cyclohexanedione, 1,2-cyclopentanedione or the like, in an inert organic solvent, e.g., tetrahydrofuran, dioxane, diethylether, dipropylether, methanol, ethanol, toluene, benzene, cyclohexane, methylene chloride or the like. The reaction is carried out at a temperature between −10° and 100° C., preferably between 0° and 70° C., and preferably in a nitrogen atmosphere.

After the reaction is terminated, the compound III thus synthesized is isolated and purified by conventional procedures, e.g., evaporation, washings, extractions, chromatography, and the like.

Compound III is then cyclized with a cyclizing reagent such as concentrated sulfuric acid, polyphosphoric acid, phosphorus pentoxide and methanesulfonic acid, or anhydrous liquid hydrogen fluoride, with anhydrous liquid hydrogen fluoride preferred. The temperature for this reaction depends on the reagent used, −10° to 10° C. for sulfuric acid and polyphosphoric acid, and −80° to 30° C., if anhydrous liquid hydrogen fluoride is used. In the preferred embodiment, a nitrogen atmosphere is used and the reaction mixture compound III and liquid hydrogen fluoride are allowed to warm up from about −80° C. to room temperature in a hood overnight.

The resulting product compound IV is recovered by neutralizing the mixture with aqueous sodium bicarbonate or other alkali, and extracting with an organic solvent, followed by conventional methods of purification, e.g., chromatography and crystallizations.

The following Preparation and Examples are illustrative of the process and the compounds of the present invention, but are not to be construed to be limiting.

In the manner given in Canadian Pat. No. 908,657, U.S. Pat. No. 3,996,230 or U.S. Pat. No. 3,734,922, 1,3-dihydro-2-hydrazino-5-(2-pyridyl)-2H-1,4-benzodiazepines can be prepared. Representative compounds, that can be thus prepared, include: 7-chloro-1,3-dihydro-2-hydrazino-5-(2-pyridyl)-2H-1,4-benzodiazepine, 7-fluoro-1,3-dihydro-2-hydrazino-5-(2-pyridyl)-2H-1,4-benzodiazepine, 7-nitro-1,3-dihydro-2-hydrazino-5-(2-pyridyl)-2H-1,4-benzodiazepine, 8-bromo-1,3-dihydro-2-hydrazino-5-(2-pyridyl)-2H-1,4-benzodiazepine, 8-fluoro-1,3-dihydro-2-hydrazino-5-(2-pyridyl)-2H-1,4-benzodiazepine, 8-chloro-1,3-dihydro-2-hydrazino-5-(2-pyridyl)-2H-1,4-benzodiazepine, 9-trifluoromethyl-1,3-dihydro-2-hydrazino-5-(2-pyridyl)-2H-1,4-benzodiazepine, 9-bromo-1,3-dihydro-2-hydrazino-5-(pyridyl)-2H-1,4-benzodiazepine, 8-nitro-1,3-dihydro-2-hydrazino-5-(2-pyridyl)-2H-1,4-benzodiazepine, 9-nitro-1,3-dihydro-2-hydrazino-5-(2-pyridyl)-2H-1,4-benzodiazepine, 7-trifluoromethyl-1,3-dihydro-2-hydrazino-5-(2-pyridyl)-2H-1,4-benzodiazepine, and the like.

EXAMPLE 1

9-Chloro-1,5-dihydro-2-methyl-1-methylene-7-phenyl-as-triazino[4,3-a][1,4]benzodiazepine (A) (7-Chloro-5-phenyl-3H-1,4-benzodiazepin-4-yl)monohydrazone of 2,3-butanedione A solution of 14.24 g. (0.05 mole) of 7-chloro-2-hydrazino-5-phenyl-3H-1,4-benzodiazepine in 200 ml. of tetrahydrofuran (under nitrogen) was cooled to 0° C. and a solution of 5.16 g. (0.06 mole) of 2,3-butanedione in 100 ml. of tetrahydrofuran was added with stirring. After 3 hours, the solution was evaporated in vacuo giving (7-chloro-5-phenyl-3H-1,4benzodiazepin-2-yl)monohydrazone of 2,3-butanedione as a light yellow noncrystalline solid.

(B) 9-Chloro-1,5-dihydro-2-methyl-1-methylene-7-phenyl-as-triazino[4,3-a][1,4]benzodiazepine A 5.5 g. (0.017 mole) portion of the above hydrazone was added, under nitrogen, to 20 ml. of liquid hydrogen fluoride at −80° C. and the solution was allowed to warm to room temperature and evaporate overnight in the hood. The residue was mixed with aqueous sodium bicarbonate, extracted with methylene chloride, washed with water, dried over sodium sulfate and evaporated in vacuo. The residue was chromatographed on silica gel, eluting with a solution consisting of 60% hexane, 35% methylene chloride and 5% 2-propanol (by volume). The product was crystallized from ethyl acetate-hexane yielding 2.04 g. (37%) of light yellow solid of melting point 190°–196° C. (dec.). A sample for analysis was recrystallized from methylene chloride-ethyl acetate, to give 9-chloro-1,5-dihydro-2-methyl-1-methylene-7-phenyl-as-triazino[4,3-a][1,4]benzodiazepine of melting point 194°–196° C.

Anal. Calcd. for $C_{19}H_{15}ClN_4$: C, 68.16; H, 4.52; Cl, 10.59; N, 16.74. Found: C, 67.99; H, 4.71; Cl, 10.69; N, 16.78.

EXAMPLE 2

9-Chloro-1,5-dihydro-2-ethyl-1-methylene-7-phenyl-as-triazino[4,3-a][1,4]benzodiazepine (A) and 9-Chloro-1,5-dihydro-1-ethylidene-2-methyl-7-phenyl-as-triazino[4,3-a][1,4]benzodiazepine (B)

In the manner given in Example 1, 2.84 g. (0.01 mole) of 7-chloro-2-hydrazino-5-phenyl-3H-1,4-benzodiazepine was condensed with 2,3-pentanedione in tetrahydrofuran. After evaporation, the residue was dissolved in methylene chloride, washed with water, dried over anhydrous sodium sulfate, evaporated and chromatographed on silica gel, eluting with hexane 70%: $CH_2Cl_2$ 25%:i-PrOH/5%. The product was an oil whose NMR (nuclear magnetic resonance) was consistent with that of a mixture of the two mono hydrazones, probably each in syn and anti forms. The yield was about 90%. This oil was added to liquid hydrogen fluoride at −80° C., allowed to evaporate overnight. Chromatography yielded two cyclized products, A and B, which were identified by NMR. Product A crystallized from ethyl-hexene giving 0.44 g. (11%) of yellow crystals which were found by melt solvate to contain 14% solvent. It had a melting point 104°–117° C. (dec.). Recrystallization from methylene chloride-ether gave an unsolvated product, namely 9-chloro-1,5-dihydro-2-ethyl-1-methylene-7-phenyl-as-triazino[4,3-a][1,4]benzodiazepine, identified by NMR (nuclear magnetic resonance spectrum) of melting point 155°–163° C. (dec.).

Product A

Anal. Calcd. for $C_{20}H_{17}ClN_4$: C, 68.86; H, 4.91; Cl, 10.16; N, 16.06. Found: C, 68.59; H, 4.88; Cl, 10.15; N, 16.01.

Product B from the column, 9-chloro-1,5-dihydro-1-ethylidene-2-methyl-7-phenyl-as-triazino[4,3-a][1,4]-benzodiazepine, was crystallized from ethyl acetatehexane giving 0.16 g. (4.6%) of yellow crystals of melting point 180°–193° C. (dec.). Identification of this product was obtained by NMR and IR (infrared spectrum).

Product B

Anal. Calcd. for $C_{20}H_{17}ClN_4$: C, 68.86; H, 4.91; Cl, 10.16; N, 16.06. Found: C, 68.73; H, 4.86; Cl, 10.34; N, 16.07.

EXAMPLE 3

11-Chloro-1,2,3,6-tetrahydro-9phenyl[1,2,4]benzotriazino[4,3-a][1,4]benzodiazepine (A) (7-Chloro-5-phenyl-3H-1,4-benzodiazepin-2-yl)monohydrazone of 1,2-cyclohexanedione To a solution of 6.59 g. (0.02 mole) of 7-chloro-2-hydrazino-5-phenyl-3H-1,4-benzodiazepine in 75 ml. of tetrahydrofuran, under nitrogen, was slowly added with stirring 2.24 g. (0.02 mole) of 1,2-cyclohexanedione. After refluxing for 4 hours, the solution was evaporated in vacuo, dissolved in methylene chloride, washed with water and dried over anhydrous sodium sulfate. Filtration and evaporation in vacuo gave (7-chloro-5-phenyl-3H-1,4-benzodiazepin-2-yl)monohydrazone of 1,2-cyclohexanedione.

(B) 11-Chloro-1,2,3,6-tetrahydro-9-phenyl[1,2,4]-benzotriazino[4,3-a][1,4]benzodiazepine This hydrazone of Example 3A was added to 20 ml. of liquid hydrogen fluoride at −80° C., and the solution was allowed to evaporate overnight in the hood. The residue was mixed with ice and sodium bicarbonate and extracted with methylene chloride. After evaporation in vacuo, the residue was chromatographed on silica gel eluting with chloroform containing 2% methanol. The product crystallized from ethyl acetate yielding 0.52 g. (7%) of yellow 11-chloro-1,2,3,6-tetrahydro-9-phenyl[1,2,4]benzotriazino[4,3-a][1,4]benzodiazepine of melting point 180°–182° C. (after softening at 130° C.). A sample for analysis, ecrystallized from methylene chloride-ethyl acetate, had the same melting point. This was shown by nmr to be an ethyl acetate solvate.

Anal. Calcd. for $C_{21}H_{17}ClN_4 \cdot \frac{1}{2}C_4H_8O_2$(ethyl acetate): C, 68.23; H, 5.23; Cl, 8.76; N, 13.84; $C_4H_8O_2$, 10.88. Found: C, 67.94; H, 5.15; Cl, 8.90; N, 13.86; $C_4H_8O_2$(by melt solvate), 11.13.

EXAMPLE 4

9-Chloro-1,5-dihydro-2-methyl-1-methylene-7-(o-chlorophenyl)-as-triazino[4,3-a][1,4]-benzodiazepine (A) [7-Chloro-5-(o-chlorophenyl)-3H-1,4-benzo-diazepin-4-yl]monohydrazone of 2,3-butane-dione In the manner given in Example 1A, 2-hydrazino-5-(o-chlorophenyl)-3H-1,4-benzodiazepine can be reacted with 2,3-butanedione to give [7-chloro-5-(o-chlorophenyl)-3H-1,4-benzodiazepin-4-yl]monohydrazone of 2,3-butanedione.

(B) 9-Chloro-1,5-dihydro-2-methyl-1-methylene-7-(o-chlorophenyl)-as-triazino[4,3-a][1,4]-benzodiazepine In the manner given in Example 1B, [7-chloro-5-(o-chlorophenyl)-3H-1,4-benzodiazepin-4-yl]monohydrazone of 2,3-butanedione can be cyclized in liquid hydrogen fluoride to give 9-chloro-1,5-dihydro-3-methyl-1-methylene-7-(o-chlorophenyl)-as-triazino[4,3-a][1,4]benzodiazepine.

EXAMPLE 5

9-Chloro-1,5-dihydro-2-ethyl-1-methylene-7-(o-fluorophenyl)-as-triazino[4,3-a][1,4]-benzodiazepine and 9-chloro-1,5-dihydro-1-ethylidene-2-methyl-7-(o-fluorophenyl)-as-triazino[4,3-a][1,4]benzodiazepine (A) [7-Chloro-5-(o-fluorophenyl)-3H-1,4-benzodiazepin-4-yl]monohydrazone of 2,3-pentanedione In the manner given in Example 1A, 7-chloro-2-hydrazino-5-(o-fluorophenyl)-3H-1,4-benzodiazepine can be reacted with 2,3-pentanedione to give a mixture of the isomeric [7-chloro-5-(o-fluorophenyl)-3H-1,4-benzodiazepin-4-yl]monohydrazones of 2,3-pentanedione.

(B) 9-Chloro-1,5-dihydro-2-ethyl-1-methylene-7-(o-fluorophenyl)-as-triazino[4,3-a][1,4]benzodiazepine and 9-chloro-1,5-dihydro-1,ethylidene-2-methyl-7-(o-fluorophenyl)-as-triazino[4,3-a][1,4]benzodiazepine In the manner given in Example 2B, the above mixture of monohydrazones of 2,3-pentanedione can be cyclized in liquid hydrogen fluoride to give 9-chloro-1,5-dihydro-2-ethyl-1-methylene-7-(o-fluorophenyl)-as-triazino[4,3-a][1,4]benzodiazepine and 9-chloro-1,5-dihydro-1-ethylidene-2-methyl-7-(o-fluorophenyl)-as-triazino[4,3-a][1,4]benzodiazepine.

EXAMPLE 6

9-Bromo-1,3-dihydro-2,5-dimethyl-1-methylene-7-(2-pyridyl)-as-triazino[4,3-a][1,4]-benzodiazepine (A) [7-Bromo-3-methyl-5-(2-pyridyl)-3H-1,4-benzodiazepin-4-yl]monohydrazone of 2,3-butanedione In the manner given in Example 1A, 7-bromo-2-hydrazino-3-methyl-5-(2-pyridyl)-3H-1,4-benzodiazepine can be reacted with 2,3-butanedione to give [7-bromo-3-methyl-5-(2-pyridyl)-3H-1,4-benzodiazepin-4-yl]monohydrazone of 2,3-butanedione.

(B) 9-Bromo-1,5-dihydro-2,5-dimethyl-1-methylene-7-(2-pyridyl)-as-triazino[4,3-a][1,4]benzodiazepine In the manner given in Example 1B, [7-bromo-3-methyl-5-(2-pyridyl)-3H-1,4benzodiazpine-4-yl]monohydrazone of 2,3-butanedione can be cyclized in liquid hydrogen fluoride to give 9-bromo-1,5-dihydro-2,5-dimethyl-1-methylene-7-(2-pyridyl)-as-triazino[4,3-a]-[1,4]benzodiazepine

EXAMPLE 7

1,5-Dihydro-2-methyl-1-methylene-7-(o-chlorophenyl)-as-triazino[4,3-a][1,4]-benzodiazepine (A) [5-(o-Chlorophenyl)-3H-1,4benzodiazepine-4-yl]monohydrazone of 2,3-butanedione In the manner given in Example 1A, 2-hydrazino-5-(o-chlorophenyl)-3H-1,4-benzodiazepine can be reacted with 2,3-butanedione to give [5-(o-chlorophenyl)-3H-1,4-benzodiazepin-4-yl]monohydrazone of 2,3-butanedione.

(B) 1,5-Dihydro-2-methyl-1-methylene-7-(o-chlorophenyl)-as-triazino[4,3-a][1,4]benzodiazepine In the manner given in Example 1B, [5-(o-chlorophenyl)-3H-1,4benzodiazepin-4-yl]monohydrazone of 2,3-butanedione can be cyclized in liquid hydrogen fluoride to give 1,5-dihydro-2-methyl-1-methylene-7-(o-chlorophenyl)-as-triazino-[4,3-a][1,4]benzodiazepine.

EXAMPLE 8

9-Trifluoromethyl-1,5-dihydro-2-methyl-1-methylene-7-phenyl-as-triazino[4,3-a][1,4]benzodiazepine (A) (7-Trifluoromethyl-5-phenyl-3H-1,4-benzodiazepine-4-yl)monohydrazone of 2,3-butanedione In the manner given in Example 1A, 7-trifluoromethyl-2-hydrazino-5-phenyl-3H-1,4-benzodiazepine can be reacted with 2,3-butanedione to give (7-trifluoromethyl-5-phenyl-3H-1,4-benzodiazepin-4-yl)monohydrazone of 2,3-butanedione.

(B) 9-Trifluoromethyl-1,5-dihydro-2-methyl-1-methylene-7-phenyl-as-triazino[4,3-α][1,4]-benzodiazepine In the manner given in Example 1B, (7-trifluoromethyl-5-phenyl-3H-1,4-benzodiazepin-4-yl)monohydrazone of 2,3-butanedione can be cyclized in liquid hydrogen fluoride to give 9-trifluoromethyl-1,5-dilhydro-2- methyl-1-methylene-7-phenyl-as-triazino[4,3-a]-[1,4]benzodiazepine.

EXAMPLE 9

9-Nitro-1,5-dihydro-2-methyl-1-methylene-7-(o-chlorophenyl)-as-triazino[4,3-a]-[1,4]-benzodiazepine (A) [7-Nitro-5-(o-chlorophenyl)-3H-1,4-benzodiazepin-4-yl]monohydrazone of 2,3-butanedione.

In the manner given in Example 1A, 9-nitro-2-hydrazino-5-(o-chlorophenyl)-3H-1,4-benzodiazepine can be reacted with 2,3-butanedione to give [7-nitro-5-(o-chlorophenyl)-3H-1,4-benzodiazepin-4-yl]monohydrazone of 2,3- butanedine.

(B) 9-Nitro-1,5-dihydro-2-methyl-1-methylene-7-(o-chlorophenyl)-as-triazino[4,3-a][1,4]benzodiazepine In the manner given in Example 1B, [7-nitro-5-(o-chlorophenyl)-3H-1,4-benzodiazepin-4-yl]monohydrazone of 2,3-butanedione can be cyclized in liquid hydrogen fluoride to give 9-nitro-1,5-dihydro-2-methyl-1-methylene-7-(o-chlorophenyl)-as-triazino[4,3-a][1,4]-benzodiazepine.

EXAMPLE 10

9-Chloro-1,5-dihydro-2-methyl-1-methylene-7-(2,6-difluorophenyl)-as-triazino[4,3-a]-[1,4]benzodiazepine (A) [7-Chloro-5-(2,6-difluorohenyl)-3H-1,4-benzodiazepin-4-yl]monohydrazone of 2,3-butanedione.

In the manner given in Example 1A, 7-chloro-2-hydrazino-5-(2,6-difluorophenyl)-3H-1,4-benzodiazepine can be reacted with 2,3-butanedione to give [7-chloro-5-(2,6-difluorophenyl)-3H1,4-benzodiazepin-4-yl]monohydrazone of 2,3-butanedione.

(B) 9-Chloro-1,5-dihydro-2-methyl-1-methylene-7-(2,6-difluorophenyl)-as-triazino[4,3-a]-[1,4]benzodiazepine.

In the manner given in Example 1B, [7-chloro-5-(2,6-difluorophenyl)-3H-1,4-benzodiazepin-4-yl]monohydrazone of 2,3-butanedione can be cyclized in liquid hydrogen fluoride to give 9-chloro-1,5-dihydro-2-methyl-1-methylene-7-(2,6-difluorophenyl)-as-triazino[4,3-a]-[1,4]benzodiazepine.

EXAMPLE 11

9-Chloro-1,5-dihydro-5-methyl-1-methylene-2-propyl-7-(o-chlorophenyl)-as-triazino[4,3-a][1,4]benzodiazepine and 9-chloro-1,5-dihydro-1,5-dimethyl-2-propylidene-7-(o-chlorophenyl)-as-triazino[4,3-a][1,4]benzodiazepine (A) [7-Chloro-5-(chlorophenyl)-3H-1,4-benzodiazepin-4-yl]-monohydrazone of 2,3-hexanedione.

In the manner given in Example 1A, 2-hydrazino-5-(o-chlorophenyl)-3-methyl-3H-1,4-benzodiazepine can be reacted with 2,3-hexanedine to give a mixture of the [7-chloro-5-(o-chlorophenyl)-3-methyl-3H-1,4-benzodiazepin-4-yl]monohydrazones of 2,3-hexanedione.

(B) 9-Chloro-1,5-dihydro-5-methyl-1-methylene-2-propyl-7-(o-chlorophenyl)-as-triazino[4,3-a][1,4]benzodiazepine and 9-chloro-1,5-dihydro-2,5-dimethyl-2-propylidene-7-(o-chlorophenyl)-as-triazino[4,3-a][1,4]benzodiazepine.

In the manner given in Example 1B, the above mixture of monohydrazones of 2,3-hexanedione can be cyclized in liquid hydrogen fluoride to give 9-chloro-1,5-dihydro-5-methyl-1-methylene-2-propyl-7-(o-chlorophenyl)-as-triazino[4,3-a][1,4]benzodiazepine and 9-chloro-1,5-dihydro-1,5-dimethyl-2-propylidene-7-(o-chlorophenyl)-as-triazino[4,3-a][1,4]benzodiazepine.

EXAMPLE 12

10-Chloro-3,6-dihydro-8-phenyl[2H]cyclopenta[-e][1,2,4]triazino[4,3-a[[1,4]benzodiazepine (A) (7-Chloro-5-phenyl-3H-1,4-benzodiazepin-4-yl)monohydrazone of 1,2-cyclopentanedione.

In the manner given in Example 3A, 7-chloro-2-hydrazino-5-phenyl-3H-1,4-benzodiazepine can be reacted with 1,2-cyclopentanedione to give (7-chloro-5-phenyl-3H-1,4-benzodiazepin-4-yl)monohydrazone of 1,2-cyclopentanedione.

(B) 10-Chloro-3,6-dihydro-8-phenyl[2H]cyclopenta[-e][1,2,4]triazino[4,3-a][1,4]benzodiazepine In the manner given in Example 3B, (7-chloro-5-phenyl-3H-1,4-benzodiazepine-4-yl)monohydrazone of 1,2-cyclopentanedione can be cyclized in liquid hydrogen fluoride to give 10-chloro-3,6-dihydro-8-phenyl-[2H]cyclopenta[e][1,2,4]triazino[4,3-a][1,4]benzodiazepine.

Example 13

10-Bromo-3,6-dihydro-8-(2-pyridyl)[2H]cyclopenta[-e][1,2,4]triazino[4,3-a][1,4]benzodiazepine (A) [7-Bromo-5-(2-pyridyl)-3H-1,4-benzodiazepin-4-yl]monohydrazone of 1,2-cyclopentanedione.

In the manner given in Example 3A, 7-bromo-2-hydrazino-5-(2-pyridyl)-3H-1,4-benzodiazepine can be reacted with 1,2-cyclopentanedione to give [7-bromo-5-(2-pyridyl)-3H-1,4-benzodiazepin-4-yl]monohydrazone of 1,2-cyclopentanedione.

(B) 10-Bromo-3,6-dihydro-8-(2-pyridyl)[2H]cyclopnta[-e][1,2,4]triazino[4,3-a][1,4]benzodiazepine.

In the manner given in Example 3B, [7-bromo-5-(2-pyridyl)-3H-1,4-benzodiazepin-4-yl]monohydrazone of 1,2-cyclopentanedione can be cyclized in liquid hydrogen fluoride to give 10-bromo-3,6-dihydro-8-(2-pyridyl)-[2H]cyclopenta[e][1,2,4]triazino[4,3-a][1,4]benzodiazepine.

EXAMPLE 14

11-Bromo-1,2,3,6-tetrahydro-9-(2-pyridyl)-[1,2,4]benzotriazino[4,3-a][1,4]benzodiazepine (A) [7-Bromo-5-(2-pyridyl)-3H-1,4-benzodiazepin-4-yl]monohydrazone of 1,2-cyclohexanedione.

In the manner given in Example 3A, 7-bromo-2-hydrazino-5-(2-pyridyl)-3H-1,4-benzodiazepine can be reacted with 1,2-cyclohexanedione to give [7-bromo-5-(2-pyridyl)-3H-1,4-benzodiazepin-4-yl]monohydrazone of 1,2-cyclohexanedione.

(B) 11-Bromo-1,2,3,6-tetrahydro-9-(2-pyridyl)-[1,2,4]benzotriazino[4,3-a[]1,4]benzodiazepine.

In the manner given in Example 3B, [7-bromo-5-(2-pyridyl)-3H-1,4-benzodiazepin-4-yl]monohydrazone of 1,2-cyclohexanedione can be cyclized in liquid hydrogen fluoride to give 11-bromo-1,2,3,6-tetrahydro-9-(2-pyridyl)-[1,2,4]benzotriazino[4,3-a][1,4]benzodiazepine.

EXAMPLE 15

10-Chloro-1,5-dihydro-5-ethyl-2-methyl-1-methylene-7-(o-fluorophenyl)-as-triazino-[4,3-a][1,4]benzodiazepine (A) [8-Chloro-3-ethyl-5-(o-fluorophenyl)-3H-1,4-benzodiazepin-4-yl]monohydrazone of 2,3-butanedione.

In the manner given in Example 1A, 8-chloro-3-ethyl-2-hydrazino-5-(o-fluorophenyl)-3H-1,4-benzodiazepine can be reacted with 2,3-butanedione to give [8-chloro-3-ethyl-5-(o-fluorophenyl)-3H-1,4-benzodiazepin-4-yl]monohydrazone of 2,3-butanedione.

(B) 10-Chloro-5-ethyl-1,5-dihydro-2-methyl-1-methylene-7-(o-fluorophenyl)-as-triazino[4,3-a][1,4]-benzodiazepine.

In the manner given in Example 1B, [8-chloro-3-ethyl-5-(o-fluorophenyl)-3H-1,4-benzodiazepin-4-yl]monohydrazone of 2,3-butanedione can be cyclized in liquid hydrogen fluoride to give 10-chloro-1,5-dihydro-5-ethyl-2-methyl-1-methylene-7-(o-fluorophenyl)-as-triazino[4,3-a][1,4]benzodiazepine.

EXAMPLE 16

11-Trifluoromethyl-1,5-dihydro-2-ethyl-1-ethylidene-7-(o-fluorophenyl)-as-triazino[4,3-a][1,4]benzodiazepine (A) [9-Trifluoromethyl-5-(o-fluorophenyl)-3H-1,4-benzodiazepin-4-yl]monohydrazone of 3,4-hexanedione.

In the manner given in Example 1A, 9-trifluoromethyl-2-hydrazino-5-(o-fluorophenyl)-3H-1,4-benzodiazepine can be reacted with 3,4-hexanedione to give [9-trifluoromethyl-5-(o-fluorophenyl)-3H-1,4-benzodiazepin-4-yl]monohydrazone of 3,4-hexanedione.

(B) 11-Trifluoromethyl-1,5-dihydro-2-ethyl-1-ethylidene-7-(o-fluorophenyl)-as-triazino[4,3-a][1,4]benzodiazepine.

In the manner given in Example 1B, [9-trifluoromethyl-5-(o-fluorophenyl)-3H-1,4-benzodiazepin-4-yl]monohydrazone of 2,3-butanedione can be cyclized in liquid hydrogen fluoride to give 11-trifluoromethyl-1,5-dihydro-2-ethyl-1-ethylidene-7-(o-fluorophenyl)-as-triazino[4,3-a][1,4]benzodiazepine.

EXAMPLE 17

8-Nitro-1,5-dihydro-2-methyl-1-methylene-7-phenyl-as-triazino[4,3-a][1,4]benzodiazepine (A) (6-Nitro-5-phenyl-3H-1,4-benzodiazepin-4-yl)monohydrazoe of 2,3-butanedione.

In the manner given in Example 1A, 6-nitro-2-hydrazino-5-phenyl-3H-1,4-benzodiazepine can be reacted with 2,3-butanedione to give (6-nitro-5-phenyl-3H-1,4-benzodiazepin-4-yl)monohydrazone of 2,3-butanedione.

(B) 8-Nitro-1,5-dihydro-2-methyl-1-metylene-7-phenyl-as-triazino[4,3-a][1,4]benzodiazepine.

In the manner given in Example 1B, (6-nitro-5-phenyl-3H-1,4-benzodiazepin-4-yl)monohydrazone of 2,3-butanedione can be cyclized in liquid hydrogen fluoride to give 8-nitro-1,5-dihydro-2-methyl-1-methylene-7-phenyl-as-triazino[4,3-a][1,4]benzodiazepine.

EXAMPLE 18

1,5-Dihydro-2-ethyl-1-methylene-7-(o-fluorophenyl)-as-triazino[4,3-a][1,4]benzodiazepine and 1,5-dihydro-1-ethylidene-2-methyl-7-(o-fluorophenyl)-as-triazino[4,3-a][1,4]benzodiazepine In the manner given in Example 2, 2-hydrazino-5-(o-fluorophenyl)-3H-1,4-benzodiazepine can be reacted with 2,3-pentanedione to give a mixture of the [5-(o-fluorophenyl)-3H-1,4-benzodiazepin-4-yl]monohydrazones of 2,3-pentanedione.

This mixture of monohydrazones of 2,3-pentanedione can be cyclized in liquid hyrogen fluoride to give 1,5-dihydro-2-ethyl-1-methylene-7-(o-fluorophenyl)-as-triazino[4,3-a][1,4]benzodiazepine and 1,5-dihydro-1-ethylidene-2-methyl-7-(o-fluorophenyl)-as-triazino-[4,3-a][1,4]benzodiazepine.

EXAMPLE 19

9-Fluoro-1,5-dihydro-1-methylene-2-propyl-7-(o-fluorophenyl)-as-triazino[4,3-a][1,4]benzodiazepine and 9-fluoro-1,5-dihydro-1-methyl-2-propylidene-7-(o-fluorophenyl)-as-triazino[4,3-a][1,4]benzodiazepine In the manner given in Example 2, 7-fluoro-2-hydrazino-5-(o-fluorophenyl)-3H-1,4-benzodiazepine can be reacted with 2,3-hexanedione to give a mixture of the [7-fluoro-5-(o-fluorophenyl)-3H-1,4-benzodiazepin-4-yl]monohydrazones of 2,3-hexanedione.

This mixture of monohydrazones of 2,3-hexanedione can be cyclized in liquid hydrogen fluoride to give 9-fluoro-1,5-dihydro-1-methylene-2-propyl-7-(o-fluorophenyl)-as-triazino[4,3-a][1,4]benzodiazepine and 9-fluoro-1,5-dihydro-1-methyl-2-propylidene-7-(o-fluorophenyl)-as-triazino[4,3-a][1,4]benzodiazepine.

EXAMPLE 20

10-Chloro-3,6-dihydro-8-(o-chlorophenyl)-[2H]-cyclopenta[e][1,2,4]triazino[4,3-a]-[1,4]benzodiazepine (A) [7-Chloro-5-(o-chlorophenyl)-3H-1,4-benzodiazepin-4-yl]monohydrazone of 1,2-cyclopentanedione.

In the manner given in Example 3A, 7-chloro-2-hydrazino-5-(o-chlorophenyl)-3H-1,4-benzodiazepine can be reacted with 1,2-cyclopentanedione to give [7-chloro-5-(o-chlorophenyl)-3H-1,4-benzodiazepin-4-yl]monohydrazone of 1,2-cyclopentanedione.

(B) 10-Chloro-3,6-dihyro-8-(o-chlorophenyl)-[2H]-cyclopenta[e][1,2,4]triazino[4,3-a][1,4]benzodiazepine.

In the manner given in Example 3B, [7-chloro-5-(o-chlorophenyl)-3H-1,4-benzodiazepin-4-yl]monohydrazone of 1,2-cyclopentanedione can be cyclized in liquid hydrogen fluoride to give 10-chloro-3,6-dihydro-8-(o-chlorophenyl)-[2H]cyclopenta[e][1,2,4]triazino-[4,3-a][1,4]benzodiazepine.

In the manner given in Example 1A, other 2-hydrazino-5-phenyl-3H-1,4-benzodiazepines can be reacted with vicinal alkane or cycloalkane diones of formula II to give the corresponding (2-hydrazino-5-phenyl-3H-1,4-benzodiazepin-4-yl)monohydrazones of the diones of formula II.

Representative diones that can be thus obtained include: (7-chloro-5-phenyl-3H-1,4-benzodiazepin-4-yl)monohydrazone of 1,2-cyclopentanedione; [7-nitro-3-ethyl-5-(o-chlorophenyl)-3H-1,4-benzodiazepin-4-yl]monohydrazone of 1,2-cyclopentanedione; ]7-trifluoromethyl-5-(o-fluorophenyl)-3H-1,4-benzodiazepin-4-yl]monohydrazone of 1,2-cyclopentanedione; (9-trifluoromethyl-5-phenyl-3H-1,4-benzodiazepin-4-yl)monohydrazone of 1,2-cyclopentanedione; (9-nitro-5-phenyl-3H-1,4-benzodiazepin-4-yl)monohydrazone of 1,2-cyclopentanedione; [8-bromo-5-(o-fluorophenyl)-3H-1,4-benzodiazepin-4-yl]monohydrazone of 1,2-cyclohexanedione; [8-nitro-3-methyl-5-(o-chlorophenyl)-3H-1,4-benzodiazepin-4-yl]monohydrazone of 1,2-cyclohexanedione; [6-chloro-5-(o-fluorophenyl)-3H-1,4-benzodiazepin-4-yl]monohydrazone of 1,2-cyclohexanedione; [7-chloro-5-(2-pyridyl)-3H-1,4-benzodiazepin-4-yl]monohydrazone of 1,3-cyclohexanedione; [9-fluoro-5-(2-pyridyl)-3H-1,4-benzodiazepin-4-yl]-monohydrazone of 1,2-cyclohexanedione; (7-nitro-5-phenyl-3H-1,4-benzodiazepin-4-yl)monohydrazone of 2,3-hexanedione; [8-nitro-5-(o-chlorophenyl)-3H-1,4-benzodiazepin-4-yl]monohydrazone of 2,3-hexanedione; [5-(o-chlorophenyl)-3H-1,4-benzodiazepin-4-yl]monohydrazone of 2,3-hexanedione; [5-(o-fluorophenyl)-3H-1,4-benzodiazepin-4-yl]monohydrazone of 2,3-hexanedione; [8-bromo-5-(o-fluorophenyl)-3H-1,4-benzodiazepin-4-yl]monohydrazone of 2,3-hexanedione; [7-bromo-5-(2-pyridyl)-3H-1,4-benzodiazepin-4-yl]monohydrazone of 2,3-hexanedione; [9-fluoro-5-(2-pyridyl)-3H-1,4-benzodiazepin-4-yl]monohydrazone of 2,3-pentanedione; [9-nitro-3-methyl-5-(2-pyridyl)-3H-1,4-benzodiazepin-4-yl]monohydrazone of 2,3-pentanedione; [6-chloro-5-(o-fluorophenyl)-3H-1,4-benzodiazepin-4-yl]monohydrazone of 2,3-pentanedione; [7-fluoro-5-(o-fluorophenyl)-3H-1,4-benzodiazepin-4-yl]monohydrazone of 2,3-butanedione; [7-trifluoromethyl-5-(o-fluorophenyl)-3H-1,4-benzodiazepin-4-yl]monohydrazone of 2,3-butanedione; and the like.

In the manner shown in Example 1B, treating the above hydrazones of formula II with liquid hydrogen fluoride produces the corresponding as-triazino[4,3-a][1,4]benzodiazepines of formula IV. Representative compounds thus obtained include: 10-chloro-3,6-dihydro-8-phenyl-[2H]cyclopenta[e][1,2,4]triazino[4,3-a][1,4]benzodiazepine; 10-nitro-6methyl-3,6-dihydro-8-(o-chlorophenyl)-[2H]cyclopenta[e][1,2,4]triazino[4,3-a][1,4]benzodiazepine; 10-trifluoromethyl-3,6-dihydro-8-(o-fluorophenyl)-[2H]cyclopenta[e][1,2,4]triazino[4,3-a][1,4]benzodiazepine; 12-trifluoromethyl-3,6-dihydro-8-phenyl-[2H]cyclopenta[e][1,2,4]triazino[4,3-a][1,4]benzodiazepine; 12-nitro-3,6-dihydro-8-phenyl-[2H]cylcopenta[e][1,2,4]triazino[4,3-a][1,4]benzodiazepine; 12-bromo-1,2,3,6-tetrahydro-9-(o-fluorophenyl)[1,2,4]benzotriazino[4,3-a][1,4]benzodiazepine; 12-nitro-1,2,3,6-tetrahydro-9-(o-chlorophenyl)-7-methyl-[1,2,4]-benzotriazino[4,3-a][1,4]benzodiazepine; 10-chloro-1,2,3,6-tetrahydro-9-(o-fluorophenyl)[1,2,4]benzotriazeino[4,3-a][1,4]benzodiazepine; 11-chloro-1,2,3,6-tetrahydro-9-(2-pyridyl)-[1,2,4]benzotriazino[4,3-a][1,4]benzodiazepine; 13-fluoro-1,2,3,6-tetrahydro-9-(2-pyridyl)[1,2,4]benzotriazino[4,3-a][1,4]benzodiazepine; 9-nitro-1,5-dihydro-1-methylene-2-propyl-7-phenyl-as-triazino-[4,3-a][1,4]benzodiazepine; 9-nitro-1,5-dihydro-2-methyl-1-propylidene-7-phenyl-as-triazino[4,3-a][1,4]benzodiazepine; 10-nitro-1,5-dihydro-1-methylene-2-propyl-7-(o-chlorophenyl)-as-triazino[4,3-a][1,4]benzodiazepine; 10-nitro-1,5-dihydro-2-methyl-1-propylidene-7-(o-chlorophenyl)-as-triazino[4,3-a][1,4]benzodiazepine; 1,5-dihydro-1-methylene-2-propyl-7-(o-chlorophenyl)-as-triazino[4,3-a][1,4]benzodiazepine; 1,5-dihydro-2-methyl-1-propyliene-7-(o-chlorophenyl)-as-triazino[4,3-a][1,4]benzodiazepine; 1,5-dihydro-1-methylene-2-propyl-7-(o-fluorophenyl)-as-triazino[4,3-a][1,4]benzodiazepine; 1,5-dihydro-2-methyl-1-propylidene-7-(o-fluorophenyl)-as-triazino[4,3-a][1,4]benzodiazepine; 10-bromo-1,5-dihydro-1-metylene-2-propyl-7-(o-fluorophenyl)-as-triazino[4,3-a][1,4]benzodiazepine; 10-bromo-1,5-dihydro-2-methyl-1-propyliene-7-(o-fluorophenyl)-as-triazino-[4,3-a][1,4]benzodiazepine; 9-bromo-1,5-dihydro-1-methylene-2-propyl-7-(2-pyridyl)-as-triazino[4,3-a][1,4benzodiazepine; 9-bromo-1,5-dihydro-2-methyl-1-propyliene-7-(2-pyridyl)-as-triazino[4,3-a][1,4]benzodiazepine; 11-fluoro-1,5-dihydro-2-ethyl-1-methylene-7-(2-pyridyl)-as-triazino[4,3-a][1,4]benzodiazepine; 11-fluoro-1,5-dihydro-1-ethylidene-2-methyl-7-(2-pyridyl)-as-triazino[4,3-a][1,4]benzodiazepine; 11-nitro-1,5-dihydro-2-ethyl-5-methyl-1-methylene-7-(2-pyridyl)-as-triazino[4,3-a[1,4]benzodiazepine; 11-nitro-1,5-dihydro-1-ethylidene-2,5-dimethyl-7-(2-pyridyl)-as-triazino[4,3-a][1,4]benzodiazepine; 8-chloro-1,5-dihydro-2-ethyl-1-methylene-7-(o-fluorophenyl)-as-triazino[4,3-a][1,4]benzodiazepine; 8-chloro-1,5-dihydro-1-ethylidene-2-methyl-7-(o-fluorophenyl)-as-triazino[4,3-a][1,4]benzodiazepine; 9-fluoro-1,5-dihydro-2-methyl-1-methylene-7-(o-fluorophenyl)-as-triazino[4,3-a][1,4]benzodiazepine; 9-trifluoromethyl-1,5-dihydro-2-methyl-1-methylene-7-(o-fluorophenyl)-as-triazino[4,3-a][1,4]benzodiazepine; and the like.

Treating the compounds of formula IV with pharamacologically acceptable acids such as hydrochloric, hydrobromic, phosphoric, sulfuric, acetic, propionic, toluenesulfonic, methanesulfonic, tartaric, citric, lactic, malic, maleic, and cyclohexanesulfamic acids produces the pharmacologically acceptable stals of these compounds of formula IV which can be used like the free base compounds of formula IV. Salt formation is achieved in conventional manner by reacting the compounds of Formula IV with excess of a selected acid in a suitable medium, e.g., water, a lower alkanol, ether, or acetone and recovering the salt by evaporating the solvent, preferably in vacuo.

We claim:

1. A compound of the formula IV:

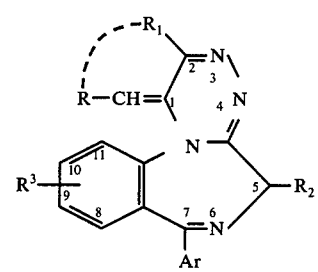

wherein R is hydrogen or alkyl of 1 to 2 carbon atoms, inclusive; wherein $R_1$ is alkyl of 1 to 3 carbon atoms, inclusive, or

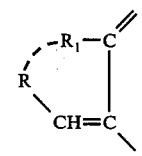

is a 2-cycloalkenylidene ring of 5 or 6 carbon atoms; wherein $R_2$ is hydrogen, methyl or ethyl; wherein $R_3$ is hydrogen, fluoro, chloro, bromo, nitro and —$CF_3$; and wherein Ar is phenyl, o-chlorophenyl, o-fluorophenyl, 2,6-difluorophenyl, and 2-pyridyl, or the pharmacologically acceptable acid addition salts thereof.

2. A compound according to claim 1 wherein R and $R_2$ are hydrogen, $R_1$ is methyl, Ar is 2-pyridyl, $R_3$ is 9-bromo, and the compound is therefore 9-bromo-1,5-dihydro-2-methyl-1-methylene-7-(2-pyridyl)-as-triazino[4,3-a][1,4]benzodiazepine.

3. A compound according to claim 1 of formula IVA:

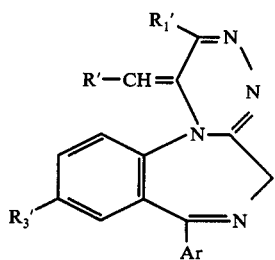

IVA wherein R' is hydrogen or methyl; wherein $R_1'$ is methyl or ethyl; wherein $R_3'$ is fluoro, chloro, bromo or trifluoromethyl; and wherein Ar is phenyl, o-chlorophenyl, o-fluorophenyl, 2,6-difluorophenyl or 2-pyridyl, or the pharmacologically acceptable acid addition salts thereof.

4. A compound according to claim 1 of formula IVB:

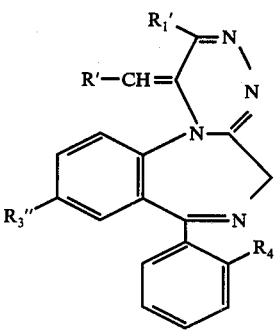

IVB wherein R' is hydrogen or methyl; wherein $R_1'$ is methyl or ethyl; wherein $R_3''$ is fluoro, chloro, or trifluoromethyl, and wherein $R_4$ is hydrogen, chloro or fluoro, or the pharmacologically acceptable acid addition salts thereof.

5. A compound according to claim 4 wherein R' is hydrogen, $R_1'$ is methyl, $R_3''$ is chloro, $R_4$ is hydrogen, and the compound is therefore 9-chloro-1,5-dihydro-2-methyl-1-metylene-7-phenyl-as-triazino[4,3-a][1,4]benzodiazepine.

6. A compound according to claim 4 wherein R' is hydrogen, $R_1'$ is methyl, $R_3''$ and $R_4$ are chloro, and the compound is therefore 9-chloro-7-(o-chlorophenyl)-1,5-dihydro-2-methyl-as-1-methylene-triazino[4,3-a]-[1,4]benzodiazepine.

7. The compound of claim 1 which is 7-(o-chlorophenyl)-1,5-dihydro-2-methyl-1-methylene-as-triazino[4,3-a][1,4]benzodiazepine.

8. A compound according to claim 4 wherein R' is hydrogen, $R_1'$ is ethyl, $R_{3'' \text{ is chloro}}$, $R_4$ is hydrogen, and the compound is therefore 9-chloro-1,5-dihydro-2-ethyl-1-methylene-7-phenyl-as-triazino[4,3-a][1,4]benzodiazepine.

9. A compound according to claim 4 wherein R' is methyl, $R_1'$ is methyl, $R_{3'' \text{ is chloro}}$, $R_4$ is hydrogen, and the compound is therefore 9-chloro-1,5-dihydro-1-ethylidene-2-methyl-7-phenyl-as-triazino[4,3-a][1,4]benzodiazepine.

10. A compound according to claim 4 wherein R' is hydrogen, $R_1'$ is ethyl, $R_3''$ is chloro, $R_4$ is chloro and the compound is therefore 9-chloro-1,5-dihydro-2-methyl-1-methylene-7-(o-chlorophenyl)-as-triazino[4,3-a][1,4]benzodiazepine.

11. A compound according to claim 4 wherein R' is methyl, $R_1'$ is methyl, $R_3''$ is chloro, $R_4$ is chloro, and the compound is therefore 9-chloro-1,5-dihyro-1-ethylidene-2-methyl-7-(o-chlorophenyl)-as-triazino[4,3-a][1,4]benzodiazepine.

12. A compound according to claim 1 wherein

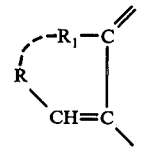

is 2-cyclohexen-1,2-ylidene, $R_3$ is 11-chloro, Ar is phenyl, $R_2$ is hydrogen, and the compound is therefore 11-chloro-1,2,3,6-tetrahydro-9-phenyl[1,2,4]benzotriazino[4,3-a][1,4]benzodiazepine.

13. A compound according to claim 1 wherein

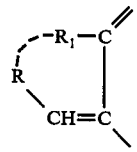

is 2-cyclopenten-1,2-ylidene, $R_2$ is hydrogen, $R_3$ is 10-chloro, Ar is phenyl, and the compound is therefore 10-chloro-3,6-dihydro-8-phenyl-[2H]cyclopenta[e][1,2,4]triazino[4,3-a][1,4]benzodiazepine.

14. A compound according to claim 1 wherein

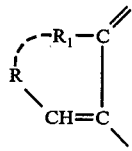

is 2-cyclopenten-1,2-ylidene, $R_2$ is hydrogen, $R_3$ is 10-bromo, Ar is 2-pyridyl, and the compound is therefore 10-bromo-3,6-dihydro-8-(2-pyridyl)[2H]cyclopenta[e][1,2,4]triazino[4,3-a][1,4]benzodiazepine.

15. A process for the production of a compound of formula IV:

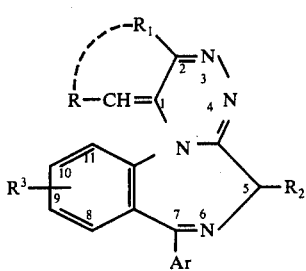

wherein R is hydrogen or alkyl of 1 to 2 carbon atoms, inclusive; wherein $R_1$ is alkyl of 1 to 3 carbon atoms, inclusive, or

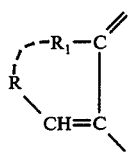

is a 2-cycloalkenylidene of 5 or 6 carbon atoms, inclusive; wherein $R_2$ is hydrogen, methyl or ethyl; wherein $R_3$ is hydrogen, fluoro, chloro, bromo, nitro and —$CF_3$; and wherein Ar is phenyl, o-chlorophenyl, o-fluorophenyl, 2,6-difluorophenyl, and 2-pyridyl, which comprises: treating a hydrazino compound of the formula:

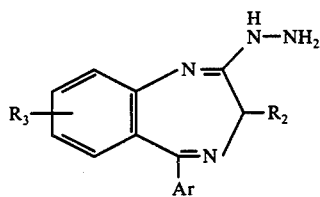

with a dicarbonyl compound II

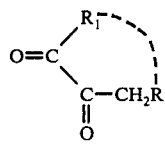

wherein R and $R_1$ are defined as above, or the group

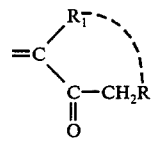

is 2-oxocyclopentylidene or 2-oxocyclohexylidene to give compound III

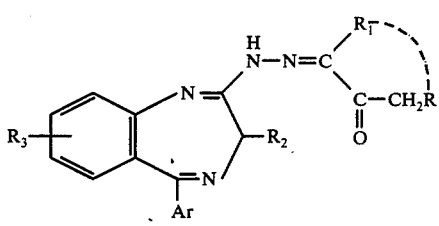

wherein R, $R_1$, $R_2$, $R_3$ and

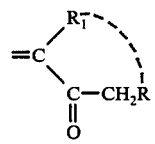

are defined as above, and treating compound II with a cyclizing agent to obtain the compound of formula IV.

16. The process of claim 15 wherein the cyclizing agent is anhydrous liquid hydrogen fluoride.

* * * * *

UNITED STATES PATENT AND TRADEMARK OFFICE
CERTIFICATE OF CORRECTION

PATENT NO. : 4,073,785

DATED : February 14, 1978

INVENTOR(S) : Gerald N. Evenson
Robert B. Moffett

It is certified that error appears in the above-identified patent and that said Letters Patent are hereby corrected as shown below:

Column 15, line 56: "1-metylene" should read -- 1-methylene --

Column 17, lines 15-25:

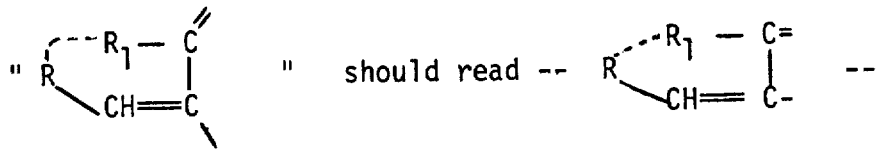

Signed and Sealed this

Twenty-sixth Day of June 1979

[SEAL]

Attest:

RUTH C. MASON
Attesting Officer

DONALD W. BANNER
Commissioner of Patents and Trademarks